US008969569B2

(12) United States Patent
Zhang et al.

(10) Patent No.: US 8,969,569 B2
(45) Date of Patent: *Mar. 3, 2015

(54) SALT AND CRYSTALLINE FORMS THEREOF OF A DRUG

(71) Applicant: AbbVie Inc., North Chicago, IL (US)

(72) Inventors: Geoff G. Z. Zhang, Libertyville, IL (US); Michael F. Bradley, Covington, WA (US); David M. Barnes, Lake Villa, IL (US); Rodger Henry, Wildwood, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/175,621

(22) Filed: Feb. 7, 2014

(65) Prior Publication Data

US 2014/0155380 A1    Jun. 5, 2014

Related U.S. Application Data

(63) Continuation of application No. 13/595,585, filed on Aug. 27, 2012, now Pat. No. 8,648,093, which is a continuation of application No. 12/763,476, filed on Apr. 20, 2010, now Pat. No. 8,273,892, which is a continuation of application No. 11/245,561, filed on Oct. 7, 2005, now Pat. No. 7,728,143, said application No. 13/595,585 is a continuation of application No. 12/701,254, filed on Feb. 5, 2010, now Pat. No. 8,252,813, which is a continuation of application No. 11/245,561.

(60) Provisional application No. 60/617,334, filed on Oct. 8, 2004.

(51) Int. Cl.
  *C07D 215/38* (2006.01)
  *A61K 31/04* (2006.01)
  *C07D 401/14* (2006.01)
  *C07C 31/26* (2006.01)

(52) U.S. Cl.
  CPC .............. *C07D 401/14* (2013.01); *C07C 31/26* (2013.01)
  USPC .......................................... 546/156; 514/312

(58) Field of Classification Search
  USPC .......................................... 546/156; 514/312
  See application file for complete search history.

(56) References Cited

U.S. PATENT DOCUMENTS

| 4,748,174 A | 5/1988 | Veronesi |
| 7,728,143 B2 * | 6/2010 | Zhang et al. ............. 546/156 |
| 8,252,813 B2 * | 8/2012 | Zhang et al. ............. 514/312 |
| 8,273,892 B2 * | 9/2012 | Zhang et al. ............. 546/156 |
| 8,648,093 B2 * | 2/2014 | Zhang et al. ............. 514/312 |
| 2003/0008899 A1 | 1/2003 | Orlandi |
| 2010/0261703 A1 | 10/2010 | Zhang et al. |

FOREIGN PATENT DOCUMENTS

| EP | 0911327 A1 | 4/1999 |
| JP | 62-252749 A | 11/1987 |
| JP | 9-511516 A | 11/1997 |
| JP | 2003-522165 A | 8/2001 |
| JP | 2002-509886 A | 4/2002 |
| JP | 2003-30882 A | 10/2003 |
| JP | 2004-168772 A | 6/2004 |
| WO | WO-97/06144 A1 | 2/1997 |
| WO | WO-01/34595 A1 | 5/2001 |

OTHER PUBLICATIONS

"ABT-492 Quinolone Antibacterial," Drugs of the Future (11): pp. 1033-1038 (2002).
Andrews, J. of Antimicrobial Chemotherapy, vol. 52, No. 3, pp. 526-527 (2003).
Chemical Abstracts Service Registry Handbook, Number Section, 2001 Supplement, CODENLCARHBT, ISSN: 0093-085X, CASE Registry No. 351422-04-3 through 356422-04-3; 352458-03-8, 21272R.
Notice of Rejection—2nd Official Action mailed by Japanese Patent Office on Mar. 6, 2012 for corresponding Japanese Patent Application No. 2007-535819 (with English translation) 6 pgs.
Published International Search Report for International Patent Application No. PCT/US2005/036024 on Jun. 22, 2006 as WO 2006/042034 A3 4 pgs.
Database Registry STN International; Aug. 23, 2001, "RN: 352458-37-8," abstract 1 pg.
Database Registry, AN 50093707, INPADOCDB, Aug. 14, 2008, "Substituted N-acyl-2-aminothiazoles," Hoffman-La Roche Inc. 2 pgs.
Database Registry, Calplus ACS on STN, AN 2006:367152, "Salt and crystalline forms thereof of a drug," Abbott Laboratories, 2006 1 pg.
Database Registry, Chemcats, Accession No. AN 2020149926, Publication Date Feb. 18, 2008, "RN 692266-90-3" 1 pg.
Database Registry, Chemcats, Accession No. AN 2030860157, Jan. 10, 2008, "RN: 692266-90-3" 1 pg.
Database Registry, INPADOCDB 2008, AN 15531230, Feb. 9, 2006, "Substituted N-Acyl-2-Aminothiazoles, Aminothiazoles Sunstitutes N-Acyl-2" Hoffmann La Roche. 4 pgs.
Database Registry, STN Entry Date May 29, 1997, CAS Registry No. 189279-58-1 2pgs.
Database Registry, STN Entry Date May 5, 2006, CAS Registry No. 883105-02-0 2pgs.
Database Registry; Chemcats Accession No. 2042828443, Ryan Scientific Screening Library catalog, Publication Date Jan. 25, 2008, CAS Registry No. 692266-90-3 1pg.
SciFinder Search Results of CAS Registry No. 352458-37-8 4 pgs, Jan. 6, 2009.

\* cited by examiner

*Primary Examiner* — D M Seaman
(74) *Attorney, Agent, or Firm* — Wilmer Cutler Pickering Hale and Dorr LLP

(57) ABSTRACT

A crystalline form of a drug, ways to make it, compositions containing it and methods of treatment of diseases and inhibition of adverse physiological events using it are disclosed.

35 Claims, 2 Drawing Sheets

SALT AND CRYSTALLINE FORMS THEREOF OF A DRUG

This application is a continuation of and claims the benefit of priority of U.S. patent application Ser. No. 13/595,585, filed Aug. 27, 2012, now U.S. Pat. No. 8,648,093 ("the '093 patent"), which is a continuation of and claims the benefit of priority of U.S. patent application Ser. No. 12/763,476, filed Apr. 20, 2010, now U.S. Pat. No. 8,273,892 ("the '892 patent"), which in turn is a continuation of and claims the benefit of priority of U.S. patent application Ser. No. 11/245,561, filed Oct. 7, 2005, now U.S. Pat. No. 7,728,143 ("the '143 patent"); the '093 patent is also a continuation of and claims the benefit of priority of U.S. patent application Ser. No. 12/701,254, filed Feb. 5, 2010, now U.S. Pat. No. 8,252,813 ("the '813 patent"), which in turn is a continuation of and claims the benefit of priority of the '143 patent; all of the foregoing of which claim priority to U.S. Provisional Patent Application Ser. No. 60/617,334, filed Oct. 8, 2004; the entire disclosures of all of the foregoing of which are incorporated by reference herein.

FIELD OF THE INVENTION

This invention pertains to a salt and crystalline forms thereof of a drug, ways to make it, compositions containing it and methods of treatment using it.

BACKGROUND OF THE INVENTION

Crystallinity of drugs effects, among other physical and mechanical properties, their solubility, dissolution rate, hardness, compressability and melting point. Because these properties may, in turn, effect a drug's manufacture and their utility, there is an existing need in the chemical and therapeutic arts for identification of crystalline forms of drugs and ways of reproducibly making them.

SUMMARY OF THE INVENTION

One embodiment of this invention pertains to D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt).

Another embodiment pertains to D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt).

Figure 1:
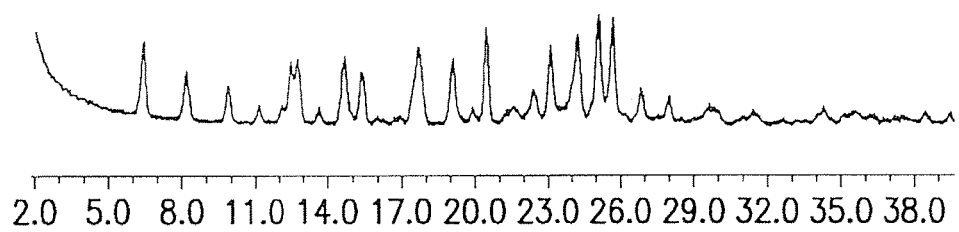
FIG. 1 shows a powder X-ray diffraction pattern of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt).

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) characterized, when measured at about 25° C. with Cu—Kα radiation, by the powder diffraction pattern shown in FIG. 1.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) characterized, in the monoclinic crystal system and P 21/C or P 21/M space group, when measured with Mo—Kα radiation at about 25° C., by respective lattice parameters a, b and c of about 16.4460 Å, 21.4010 Å and 5.3050 Å and α of about 109°.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) having substantial crystalline purity and characterized, when measured at about 25° C. with Cu—Kα radiation, by the powder diffraction pattern shown in FIG. 1.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) having substantial crystalline purity and characterized, in the monoclinic crystal system and P 21/C or P 21/M space group, when measured with Mo—Kα radiation at about 25° C., by respective lattice parameters a, b and c of about 16.4460 Å, 21.401 Å and 5.3050. Å and β of about 109°.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) having substantial crystalline purity and substantial chemical purity and characterized, when measured at about 25° C. with Cu—Kα radiation, by the powder diffraction pattern shown in FIG. 1.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) having substantial crystalline purity and substantial chemical purity and characterized, in the monoclinic crystal system and P 21/C or P 21/M space group, when measured with Mo—Kα radiation at about 25° C., by respective lattice parameters a, b and c of about 16.4460 Å, 21.4010 Å and 5.3050 Å and 0 of about 109°.

Still another embodiment pertains to a composition comprising an excipient and a therapeutically acceptable amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) characterized, when measured at about 25° C. with Cu—Kα radiation, by the powder diffraction pattern shown in FIG. 1.

Still another embodiment pertains to a composition comprising an excipient and a therapeutically acceptable amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) characterized, in the monoclinic crystal system and P 21/C or P 21/M space group, when measured with Mo—Kα radiation at about 25° C., by respective lattice parameters a, b and c of about 16.4460 Å, 21.4010 Å and 5.3050 Å and 0 of about 109°.

Still another embodiment pertains to a method for treating bacterial infections in a fish or a mammal comprising administering thereto a therapeutically effective amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt)

characterized, when measured at about 25° C. with Cu—Kα radiation, by a powder diffraction pattern shown in FIG. 1.

Still another embodiment pertains to a method for treating bacterial infections in a fish or a mammal comprising administering thereto a therapeutically effective amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) characterized, in the monoclinic crystal system and P 21/C or P 21/M space group, when measured with Mo—Kα radiation at about 25° C., by respective lattice parameters a, b and c of about 16.4460 Å, 21.4010 Å and 5.3050 Å and 0 of about 109°.

Figure 2:
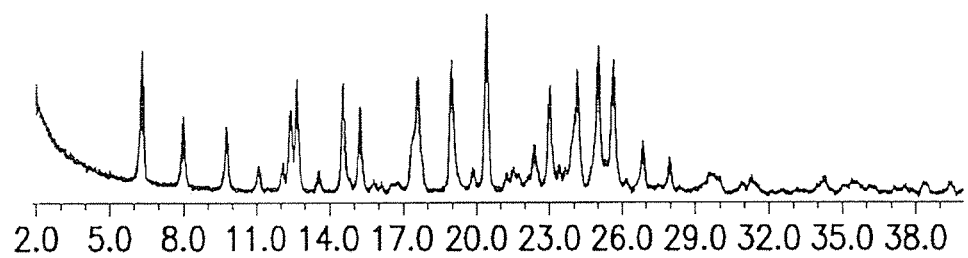
FIG. 2 shows a powder X-ray diffraction pattern of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt).

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) characterized, when measured at about 25° C. with Cu—Kα radiation, by the powder diffraction pattern shown in FIG. 2.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) characterized, in the monoclinic crystal system and P 21/C or P 21/M space group, when measured with Mo—Kα radiation at about 25° C., by respective lattice parameters a, b and c of about 8.2490 Å, 29.9840 Å and 12.5070 Å and 0 of about 105°.

Still another embodiment pertains to a crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) having substantial crystalline purity and characterized, when measured at about 25° C. with Cu—Kα radiation, by the powder diffraction pattern shown in FIG. 2.

Still another embodiment pertains to a crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) having substantial crystalline purity and characterized, in the monoclinic crystal system and P 21/C or P 21/M space group, when measured with Mo—Kα radiation at about 25° C., by respective lattice parameters a, b and c of about 8.2490 Å, 29.9840 Å and 12.5070 Å and 0 of about 105°.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) having substantial crystalline purity and substantial chemical purity and characterized, when measured at about 25° C. with Cu—Kα radiation, by the powder diffraction pattern shown in FIG. 2.

Still another embodiment pertains to crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) having substantial crystalline purity and substantial chemical purity and characterized, in the monoclinic crystal system and P 21/C or P 21/M space group, when measured with Mo—Kα radiation at about 25° C., by respective lattice parameters a, b and c of about 8.2490 Å, 29.9840 Å and 12.5070 Å and 0 of about 105°.

Still another embodiment pertains to a composition comprising an excipient and a therapeutically acceptable amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) characterized, when measured at about 25° C. with Cu—Kα radiation, by the powder diffraction pattern shown in FIG. 2.

Still another embodiment pertains to a composition comprising an excipient and a therapeutically acceptable amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) characterized, in the monoclinic crystal system and P 21/C or P 21/M space group, when measured with Mo—Kα radiation at about 25° C., by respective lattice parameters a, b and c of about 8.2490 Å, 29.9840 Å and 12.5070 Å and 0 of about 105°.

Still another embodiment pertains to a method for treating bacterial infections in a fish or a mammal comprising administering thereto a therapeutically effective amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) characterized, when measured at about 25° C. with Cu—Kα radiation, by a powder diffraction pattern shown in FIG. 2.

Still another embodiment pertains to a method for treating bacterial infections in a fish or a mammal comprising administering thereto a therapeutically effective amount of crystalline D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) characterized, in the monoclinic crystal system and P 21/C or P 21/M space group, when measured with Mo—Kα radiation at about 25° C., by respective lattice parameters a, b and c of about 8.2490 Å, 29.9840 Å and 12.5070 Å and β of about 105°.

Still another embodiment pertains to a process for making D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate (salt) comprising dehydrating D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt).

Still another embodiment pertains to D-glucitol, 1-deoxy-1-(methylamino)-,1-(6-amino -3,5-difluoropyridin-2-yl)-8-chloro-6-fluoro-1,4-dihydro-7-(3-hydroxyazetidin-1-l) -4-oxo-3-quinolinecarboxylate (salt) prepared as described in the preceding embodiment.

Still another embodiment pertains to a process for making D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) by crystallization of D-glucitol, 1-deoxy-1-(methylamino)-, 1-(6-amino-3,5-difluoro2-pyridinyl)-8-chloro-6-fluoro-1,4-dihydro-7-(3-hydroxyazendin-1-yl)-4-oxo-3-quinolinecarboxylate (salt) from water, with or without alcohol.

Still another embodiment pertains to D-glucitol, 1-deoxy-1-(methylamino)-, 1-(6-amino -3,5-difluoropyridin-2-yr)-8-chloro-6-fluoro-1,4-dihydro-7-(3-hydroxyazetidin-1-yl)-4-oxo-3-quinolinecarboxylate trihydrate (salt) prepared as described in the preceding embodiment.

DETAILED DESCRIPTION OF THE INVENTION

The term "alcolol," as used herein, means a compound having formula $R^1OH$, wherein $R^1$ is $C_1$-alkyl, $C_2$-alkyl, $C_3$-alkyl, $C_4$-alkyl, $C_5$-alkyl or $C_6$-alkyl.

The term "$C_1$-alkyl," as used herein, means methyl.

The term "C$_2$-alkyl," as used herein, means ethyl.

The term "C$_3$-alkyl," as used herein, means prop-1-yl and prop-2-yl (isopropyl).

The term "C$_4$-alkyl," as used herein, means but-1-yl, but-2-yl, 2-methylprop-1-yl and 2-methylprop-2-yl (tert-butyl).

The term "C$_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "C$_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "crystalline," as used herein, means having a regularly repeating arrangement of molecules or external face planes.

The term "substantial crystalline purity," as used herein, means at least about 95% crystalline purity, preferably about 97% crystalline purity, more preferably about 99% crystalline purity, and most preferably about 100% crystalline purity.

The term "crystalline purity," as used herein, means percentage of a crystalline compound in a sample which may contain an amorphous form of the same compound, at least one other crystalline form of the compound or a mixture thereof.

The term "substantial chemical purity," as used herein, means about 95% chemical purity, preferably about 97% chemical purity, more preferably about 98% chemical purity, and most preferably about 100% chemical purity.

The term "chemical purity," as used herein, means percentage of a particular compound in a sample.

Unless stated otherwise, percentages stated throughout this specification are weight/weight (w/w) percentages.

The term "amorphous," as used herein, means essentially without regularly repeating arrangement of molecules or external face planes.

The term "mixture," as used herein, means a combination of at least two substances, in which one substance may be completely soluble, partially soluble or essentially insoluble in the other substance.

The term "solvent," as used herein, means a substance, preferably a liquid or a miscible, partially miscible or immiscible mixture of two or more liquids, which is capable of completely dissolving, partially dissolving, dispersing or partially dispersing another substance, preferably a solid or a mixture of solids.

The term "anti-solvent," as used herein, means a solvent in which a compound is essentially insoluble.

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

It is meant to be understood that peak heights in a powder x-ray diffraction pattern may vary and will be dependent on variables such as the temperature, crystal size, crystal habit, sample preparation or sample height in the analysis well of the Scintag$^x$2 Diffraction Pattern System.

It is also meant to be understood that peak positions may vary when measured with different radiation sources. For example, Cu—K$\alpha_i$, Mo—K$\alpha$, Co—K$\alpha$ and Fe—K$\alpha$ radiation, having wavelengths of 1.54060 Å, 0.7107 Å, 1.7902 Å and 1.9373 Å, respectively, may provide peak positions which differ from those measured with Cu—K$\alpha$ radiation.

While digital outputs from powder x-ray diffractometers may be set to express peak positions to the one-hundredth and one-thousandth of a degree past the decimal, diffractometers are incapable of accurate experimental determination beyond one-tenth of a degree. Accordingly, peak positions reported herein are rounded to one-tenth of a degree past the decimal.

Compositions made with or comprising a crystalline compound of this invention may be administered, for example, bucally, ophthalmically, orally, osmotically, parenterally (intramuscularly, intrasternally, intravenously, subcutaneously), rectally, topically, transdermally or vaginally. Ophthalmically administered dosage forms may be administered as, for example, elixirs, emulsions, microemulsions, ointments, solutions, suspensions or syrups. Orally administered solid dosage forms may be administered as, for example, capsules, dragees, emulsions, granules, pills, powders, solutions, suspensions, tablets, microemulsions, elixirs, syrups or powders for reconstitution. Osmotically and topically administered dosage forms may be administered as, for example, creams, gels, inhalants, lotions, ointments, pastes or powders. Parenterally administered dosage forms may be administered, as, for example, aqueous or oleaginous suspensions. Rectally and vaginally dosage forms may be administered, for example, as creams, gels, lotions, ointments or pastes.

The therapeutically acceptable amount of a crystalline compound of this invention depends on recipient of treatment, disorder being treated and severity thereof, composition containing it, time of administration, route of administration, duration of treatment, its potency, its rate of clearance and whether or not another drug is co-administered. The amount of a crystalline compound of this invention used to make a composition to be administered daily to a patient in a single dose or in divided doses is from about 0.03 to about 200 mg/kg body weight. Single dose compositions contain these amounts or a combination of submultiples thereof A crystalline compound of this invention may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions made with or comprising a crystalline compound of this invention to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions made with a crystalline compound of this invention to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof.

Excipients for preparation of compositions made with a crystalline compound of this invention to be administered osmotically include, for example, chlorofluorohydrocarbons, ethanol, water and mixtures thereof. Excipients for preparation of compositions made with a crystalline compound of this invention to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions made with or comprising a crystalline compound of this invention to be administered rectally or vaginally include, for example, cocoa butter, polyethylene glycol wax and mixtures thereof Solubilities of 1-(6-amino-3,5-difluoropyridin-2-yl)-8-chloro-6-fluoro-1,4-dihydro-7-(3-hydroxyazetidin-1-yl)-4-oxo-3-quinolinecarboxylic acid in different buffered solutions at 25° C. are shown in TABLE 1.

TABLE 1

| Medium | Final pH | Solubility (mg/mL) |
| --- | --- | --- |
| saline | 5.8-5.9 | 0.013 |
| 0.1 HCl | 0.8 | 0.00326 |
| citrate buffer 4.0 | 4.2 | 0.00344 |
| citrate buffer 5.0 | 5.1 | 0.00333 |
| phosphate buffer 6.8 | 6.8 | 0.0668 |
| phosphate buffer 7.4 | 7.4 | 0.283 |
| Phosphate Buffer 8.0 | 7.8 | 0.651 |
| glycine buffer 9.0 | 8.2 | 2.49 |
| 0.1M NaOH | 8.4 | 3.40 |
| ethanol | — | 0.867 |

Solubilities of 1-(6-amino-3,5-difluoropyridin-2-yl)-8-chloro-6-fluoro-1,4-dihydro-7-(3-hydroxyazetidin-1-yl)-4-oxo-3-quinolinecarboxylic acid in different base solutions at 25° C. are shown in TABLE 2.

TABLE 2

| Base solution | Solubility (mg/mL) | $K_{sp}(M^2)$ | $S_{water}$ (mg/mL) |
| --- | --- | --- | --- |
| 1M NaOH | 8.33 | $1.66 \times 10^{-2}$ | 56.8 |
| 0.5M KOH | 24.4 | $1.69 \times 10^{-2}$ | 57.4 |
| 1.0M TRIS | 5.76 | $1.619 \times 10^{-4}$ | 4.8 |
| 1M L-arginine | 11.2 | $4.81 \times 10^{-4}$ | 9.67 |
| 1M meglumin | 32.1 | $2.81 \times 10^{-3}$ | 23.6 |
| 1M ethanolamine | 24.9 | $2.04 \times 10^{-3}$ | 19.9 |

The solubility of D-glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate trihydrate (salt) in different base solutions at 25° C. is shown in TABLE 3.

TABLE 3

| Medium | Final pH | Solubility (mg/mL) | $K_{sp}(M^2)$ |
| --- | --- | --- | --- |
| water | 8.78 | 33.9 | $5.00 \times 10^{-3}$ |
| 0.01M meglumine | 9.00 | 32.4 | $4.71 \times 10^{-3}$ |
| 0.1M meglumine | 9.83 | 32.2 | $4.16 \times 10^{-3}$ |
| 1M meglumine | 10.85 | 30.8 | $3.34 \times 10^{-3}$ |

The data in TABLES 1, 2 and 3 show the solubility effect of the counterion of 1-(6-amino-3,5-difluoropyridin-2-yl)-8-chloro-6-fluoro-1,4-dihydro-7-(3-hydroxyazetidin-1-yl)-4-oxo-3-quinolinecarboxylic acid.

The following examples are presented to provide what is believed to be the most useful and readily understood description of procedures and conceptual aspects of this invention.

EXAMPLE 1

A mixture of 1-(6-amino-3,5-difluoro2-pyridinyl)-8-chloro-6-fluoro-1,4-dihydro-7-(3-hydroxyazetidin-1-yl)-4-oxo-3-quinolinecarboxylate (50 Kg) and 1-deoxy-1-(methylamino)-D-glucitol (26.1 Kg) was diluted with water (75.5 Kg) and isopropanol (60.2 Kg), stirred at 45° C., cooled to 30±5° C., treated with isopropanol (175.7 Kg) while maintaining the internal temperature at about 30° C. and filtered. The filtrant was washed with isopropanol and dried under reduced pressure at 30° C. for 12 hours then at 50° C. mp; 170-172° C. $^1$H ($D_2O$/500 MHz) 8.22 (d, J=0.76 Hz, 1H), 7.71 (d, J=14.19 Hz, 1H), 7.52 (dd, J=9.31, 0.77 Hz, 1H), 4.58 (m, 2H), 4.53 (m, 1H), 4.15 (m, 3H), 3.83 (m, 2H), 3.774 (m, 1H), 3.662 (m, 2H), 3.2 (m, 2H), 2.79 (s, 3H).

EXAMPLE 2

A mixture of 1-(6-amino-3,5-difluoro2-pyridinyl)-8-chloro-6-fluoro-1,4-dihydro-7-(3-hydroxyazetidin-1-yl)-4-oxo-3-quinolinecarboxylate (29.6 Kg) and 1-deoxy-1-(methylamino)-D-glucitol (18.4 Kg) was diluted with water (133 Kg), stirred at 60° C. until all solids dissolved, cooled to 38° C. and held there until solid formed, cooled to 0° C. and filtered. The filtrant was washed with isopropanol and dried at 50° C.

The foregoing is merely illustrative of the invention and is not intended to limit the same to disclosed embodiments. Variations and changes obvious to one skilled in the art are intended to be within the scope and nature of the invention as defined in the appended claims.

What is claimed is:

1. A therapeutic composition comprising D-Glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl)-4-oxo-3-quinolinecarboxylate salt, at least one filler, at least one binder, at least one disintegrating agent, at least one buffering agent and at least one lubricant.

2. The composition of claim 1, wherein the salt is present in a therapeutically acceptable amount.

3. The composition of claim 1, wherein the salt is crystalline.

4. The composition of claim 3, wherein the salt has substantial crystalline purity.

5. The composition of claim 4, wherein the salt has at least about 95% crystalline purity.

6. The composition of claim 3, wherein the salt is characterized, when measured at about 25° C. with Cu-Kα radiation, by the powder diffraction pattern shown in FIG. 1.

7. The composition of claim 3, wherein the salt is characterized by respective lattice parameters, a, b, and c of about 16.4460 Å, 21.4010 Å, and 5.3050 Å and β of about 109° in the monoclinic crystal system P 21/C or P 21/M space group, when measured with Mo-Kα radiation at about 25° C.

8. The composition of claim 1, wherein the salt has substantial chemical purity.

9. The composition of claim 8, wherein the salt is about 97% chemically pure.

10. The composition of claim 8, wherein the salt is about 98% chemically pure.

11. The composition of claim 8, wherein the salt is about 100% chemically pure.

12. The composition of claim 1, wherein the composition is an orally administered dosage form.

13. The composition of claim 1, wherein the at least one filler comprises cellulose.

14. The composition of claim 1, wherein the at least one binder comprises povidone.

15. The composition of claim 1, wherein the at least one disintegrating agent comprises cross-povidone.

16. The composition of claim 1, wherein the at least one buffering agent comprises a sodium phosphate salt.

17. The composition of claim 1, wherein the at least one buffering agent comprises a citrate.

18. The composition of claim 1, wherein the at least one lubricant comprises magnesium stearate.

19. The composition of claim 1, wherein the at least one filler comprises cellulose, the at least one binder comprises povidone, the at least one disintegrating agent comprises cross-povidone, the at least one buffering agent comprises a sodium phosphate salt, and the at least one lubricant comprises magnesium stearate.

20. The composition of claim 19, further comprising a citrate.

21. A therapeutic composition comprising D-Glucitol, 1-deoxy-1-(methylamino)-, 1-(6-amino-3,5-difluoropyridin-2-yl)-8-chloro-6-fluoro-1,4-dihydro-7-(3-hydroxyazetidin-1-yl) -4-oxo-3-quinolinecarboxylate salt, cellulose, povidone, cross-povidone, a sodium phosphate salt and magnesium stearate.

22. The therapeutic composition of claim 21, further comprising a citrate.

23. A method of treating a bacterial infection in a fish or a mammal comprising administering thereto a composition comprising a therapeutically acceptable amount of D-Glucitol, 1-deoxy-1-(methylamino)-, 1-(6-amino-3,5-difluoropyridin-2-yl) -8-chloro-6-fluoro-1,4-dihydro-7-(3-hydroxyazetidin-1-yl)-4-oxo-3-quinolinecarboxylate salt, at least one filler, at least one binder, at least one disintegrating agent, at least one buffering agent and at least one lubricant.

24. The method of claim 21, wherein the composition is administered to a mammal.

25. The method of claim 21, wherein the therapeutically acceptable amount is from about 0.03 to about 200 mg/kg body weight.

26. The method of claim 21, wherein the at least one filler comprises cellulose.

27. The method of claim 21, wherein the at least one binder comprises povidone.

28. The method of claim 21, wherein the at least one disintegrating agent comprises cross-povidone.

29. The method of claim 21, wherein the at least one buffering agent comprises a sodium phosphate salt.

30. The method of claim 21, wherein the at least one buffering agent comprises a citrate.

31. The method of claim 21, wherein the at least one lubricant comprises magnesium stearate.

32. The method of claim 21, wherein the at least one filler comprises cellulose, the at least one binder comprises povidone, the at least one disintegrating agent comprises cross-povidone, the at least one buffering agent comprises a sodium phosphate salt, and the at least one lubricant comprises magnesium stearate.

33. The method of claim 32, further comprising a citrate.

34. A method of treating a bacterial infection in a fish or a mammal comprising administering thereto a composition comprising a therapeutically acceptable amount of D-Glucitol, 1-deoxy-1-(methylamino)-, 1-(6-amino-3,5-difluoropyridin-2-yl)-8-chloro-6-fluoro-1,4-dihydro -7-(3-hydroxyazetidin-1-yl)-4-oxo-3-quinolinecarboxylate salt, at least one filler, cellulose, povidone, cross-povidone, a sodium phosphate salt and magnesium stearate.

35. The method of claim 34, further comprising a citrate.

\* \* \* \* \*